United States Patent [19]

Olah

[11] Patent Number: 4,613,723

[45] Date of Patent: Sep. 23, 1986

[54] PROCESS FOR EFFECTING HYDROCARBON ISOMERIZATION OR ALKYLATION

[75] Inventor: George A. Olah, Beverly Hills, Calif.

[73] Assignee: PCUK-Produits Chimiques Ugine Kuhlmann, Courbevoie, France

[21] Appl. No.: 568,273

[22] Filed: Jan. 3, 1984

Related U.S. Application Data

[60] Continuation-in-part of Ser. No. 164,950, Jul. 1, 1980, abandoned, which is a division of Ser. No. 23,676, Mar. 26, 1979, abandoned.

[51] Int. Cl.$^4$ ............................ C07C 2/58; C07C 5/13
[52] U.S. Cl. ................................. 585/730; 585/747; 585/458; 585/474
[58] Field of Search ................ 585/458, 474, 730, 747

[56] References Cited

U.S. PATENT DOCUMENTS 4,288,646  9/1981  Olah ...................................... 585/458
4,339,613  7/1982  Olah ...................................... 568/768
4,339,614  7/1982  Olah ...................................... 568/768
4,423,254  12/1983 Olah ...................................... 568/781
4,424,382  1/1984  Olah ...................................... 568/783
4,503,263  3/1985  Olah ...................................... 568/594
4,547,474  10/1985 Olah ...................................... 502/168
4,547,604  10/1985 Olah ...................................... 585/477
4,547,606  10/1985 Olah ...................................... 585/458

Primary Examiner—Curtis R. Davis
Attorney, Agent, or Firm—Pennie & Edmonds

[57] ABSTRACT

The present invention relates to supported superacidic catalysts comprising $C_4$–$C_{18}$, preferentially $C_6$ to $C_{12}$, perfluorinated alkanesulfonic acid absorbed on suitable supports, such as fluoridated alumina, alumina silica and other chalcides having bonded thereto subsequently a Lewis acid compound selected from the higher valency fluorides of the elements of Groups IIA, IIIA, IVB, VA or VIB of the Periodic Table. The invention includes a process for catalytic transformation of hydrocarbons.

12 Claims, No Drawings

PROCESS FOR EFFECTING HYDROCARBON ISOMERIZATION OR ALKYLATION

This application is a continuation-in-part of Ser. No. 164,950, filed July 1, 1980, abandoned, which is a divisional application of Ser. No. 23,676, filed Mar. 26, 1979, abandoned.

BACKGROUND OF THE INVENTION

For a century Friedel-Crafts type reactions were carried out in solution using $AlCl_3$ and related Lewis acid halide type catalysts. These reactions, some of which gained very significant industrial application, such as the ethylation of benzene, the isobutylation of isobutylene, the isomerization of hydrocarbons, are all well recognized to involve the formation of highly colored complex layers (so called "red oils"). Decomposition of the complex layers necessitates additional steps and generally results in the loss of the catalyst.

The realization of the nature of the Friedel-Crafts reactions and their catalyst resulted in an understanding of the generalized acid catalyzed characteristics of these reactions, and allowed the use of a large variety of not only Lewis, but of Bronsted acid type catalyst systems. The use of supported solid acid catalysts, allowing catalytic heterogeneous reactions, was, until recently, of limited scope. They were utilized only in specific instances, such as in the preparation of cumene via propylation of benzene with propylene, using catalysts of the supported solid phosphoric acid type. Similar reaction conditions for the preparation of ethylbenzene from benzene and ethylene were found less satisfactory. Ethylation was observed to take place only at higher temperatures, and, even more significantly, the transethylation of benzene with di- or polyethylbenzenes inevitably formed in the reactions, is not satisfactorily realized under heterogeneous catalytic conditions.

Friedel-Crafts isomerization of hydrocarbons, such as of alkanes to highly branched isomeric mixtures or the isomerization of dialkylbenzenes, such as xylenes, was also until now predominantly carried out with liquid Friedel-Crafts catalyst systems, such as $AlBr_3$, $AlCl_3$, $HF-BR_3$, and the like.

The formation of complexes with $AlCl_3$, or related catalysts, generally necessitate the use of molar excess of "catalyst" as well as decomposition of stable catalyst-product complexes, and limit the industrial and practical use of liquid phase Friedel-Crafts reactions compared with other catalytic systems, such as metal and organometallic catalyzed transformation reactions, isomerization, and the like.

It is on this basis, consequently, that there is substantial practical significance in this invention to modify the usual Friedel-Crafts type reactions in a way, which can be described on the basic principle, to utilize high acidity supported catalysts, in which the acidity is provided by a higher perfluorinated alkanesulfonic acid ($C_nF_{2n+1}SO_3H$; $n=4-18$) bonded to a higher valence metal fluoride, preferentially antimony pentafluoride, tantalum pentafluoride or niobium pentafluoride.

Liquid superacid catalysts, such as magic acid, $FSO_3H-SbF_5$, fluoroantimonic acid, $HF-SbF_5$ or $CF_3SO_3H-SbF_5$ have estimated acidities on the logarithmic Hammett acidity scale reading up to about $-25$ (as compared with $-11$ for 100% sulfuric acid, or $-10$ for 100% HF) and are, thus, up to $10^{14}$ times stronger than conventional strong mineral acids.

The solution chemistry of superacids was well documented in recent years. It was based on this background that it was attempted to attach these superacid systems to suitable solid supports. Difficulties in achieving this goal are, however, significant. For example, $BF_3$ based systems such as the $HF-BF_3$, cannot be efficiently absorbed onto solid supports because of the great ease with which $BF_3$ (as well as HF) is desorbed from these solid supports. $AsF_5$, $SbF_5$, $TaF_5$, $NbF_5$, having lower vapor pressures and increased ability for fluorine-bridging, are somewhat more adaptable to be attached to solid supports. Due to the extreme chemical reactivity of $SbF_5$, and related higher valency metal fluorides, it was found that they can be attached only satisfactorily to fluorinated carriers, such as fluoridated alumina.

$SbF_5-FSO_3H$ (magic acid) or $SbF_5-CF_3SO_2H$ on fluoridated-alumina, at 70°, isomerizes straight chain alkanes such as n-heptane, or n-hexane. (U.S. Pat. No. 3,766,286) or catalyzes the alkylation of alkanes or aromatic hydrocarbons (U.S. Pat. No. 3,708,553).

Trifluoromethanesulfonic acid ($CF_3SO_3H$)—$SbF_5$ supported catalyst was disclosed for the hydroisomerization of paraffins (U.S. Pat. No. 3,878,261) but the prior art does not teach or disclose the use of higher perfluorinated alkanesulfonic acids in solid superacidic catalyst compositions. This is understandable since one would expect the acidity of the higher perfluorinated alkanesulfonic acids to decrease to a significant extent. Supported $SbF_5-FSO_3H$ or $SbF_5-CF_3SO_3H$ catalysts are effective for isomerization and alkylation reactions, but show limited adherence of the catalyst to the surface, mostly due to the relative volatility of fluorosulfuric or trifluoromethanesulfonic acid.

$SbF_5$, $NbF_5$ and $TaF_5$ based superacids can also be deposited on inert polyfluorinated polymer supports (Teflon, Kel-F and the like) or on fluorinated polycarbon (coke). Adherence to these surfaces, however, is also limited. They can also be intercolated into graphite of fluorinated graphite (as in U.S. Pat. No. 4,116,880) but these catalysts utilize only surface exposed acids and not those maintained in the graphite layers.

SUMMARY OF THE INVENTION

The present invention relates to supported superacidic catalysts comprising $C_4$-$C_{18}$, preferentially $C_6$ to $C_{12}$, perfluorinated alkanesulfonic acid absorbed on suitable supports, such as fluoridated alumina, alumina silica and other chalcides having bonded thereto subsequently a Lewis acid compound selected from the higher valency fluorides of the elements of Groups IIA, IIIA, IVB, VA or VIB of the Periodic Table. The invention includes a process for catalytic transformation of hydrocarbons.

The present catalyst system based on supported solid perfluorinated alkanesulfonic acids of extremely low volatility has catalytic activity of extended duration in comparison to previously known supported catalysts. The catalyst systems also unexpectedly have high acidity.

DETAILED DESCRIPTION OF THE INVENTION

The present catalytic process for hydrocarbon transformation requires the presence of a heterogeneous catalyst comprising $C_4$ to $C_{18}$ perfluorinated alkanesulfonic acid, which has bound to it a higher valency Lewis acid fluoride $MF_n$, wherein M is a metal selected from the metals of the Groups II to VI of the Periodic Table and n is compatible with the valance of the metal M. These catalysts were found to be of high activity and long duration. The Lewis acid halides are well known to those skilled in the art and are represented by compounds such as antimony pentafluoride, niobium pentafluoride, tantalum pentafluoride, titanium tetrafluoride, bismuth pentafluoride, molybdenum hexafluoride, arsenic pentafluoride, phosphorous pentafluoride and the like. The amount of Lewis acid bound to the perfluorinated alkanesulfonic acids is generally from between about 1 and 50 percent by weight of the total catalyst composition. The bonding of the Lewis acid halides to the perfluorinated alkanesulfonic acid is readily effected by reacting the perfluorinated alkanesulfonic acids deposited or absorbed on a suitable carrier with the Lewis acid fluorides at a temperature of between about 20° and 300° C., preferentially between about 80° and 200° C., by distilling the Lewis acid fluoride, if needed, in vacuum, onto the perfluorinated sulfonic acid.

Alkylation and isomerization, as well as de- and transalkylations, disproportionation, polymerization, cracking and related processes of hydrocarbons, are readily catalyzed with the catalysts of the present invention as described herein. These processes are effected by contacting a charge of a hydrocarbon, or hydrocarbon mixture with the above described catalysts under the conventional conditions of the desired hydrocarbon conversion. Contacting of the catalyst with the hydrocarbon charge is facilitated by using such conventional systems as fixed bed systems, moving bed systems, fluidized bed systems, continuous or batch-type operations. The hydrocarbon conversions utilizing the presently described catalysts can be carried out either in the vapor phase, in the liquid phase, or as mixed phase operations. Conversions can be also carried out in the presence of hydrogen, or naphthenic hydrocarbons as moderators, which tend to decrease any concurrent cracking reactions. Operation in the presence of hydrogen and related hydrocarbon moderators are particularly advantageous for isomerizations. In these instances, Lewis acid halides with high redox potentials are preferred, such as tantalum pentafluoride, niobium pentafluoride and the like, over more readily reducible halides, such as antimony pentafluoride.

Isomerization of isomerizable $C_4$ to $C_{30}$ hydrocarbons, such as paraffins, naphthenes or alkyl-aromatic hydrocarbons may be effectively carried out utilizing the catalysts of this invention. Isomerization of straight-chain or slightly branched-chain paraffins containing 4 or more carbon atoms in their molecules, such as n-butane, n-pentane, n-hexane, n-heptane, n-octane, and the like, may be readily effected. Likewise, cycloparaffins containing at least 5 carbon atoms in the ring, such as alkyl cyclopentanes and cyclohexanes may be effectively isomerized. These isomerizations are particularly suitable to produce high octane number branched paraffin mixtures of the gasoline range. As examples of commercial mixtures, straight-run type or light naphtha fractions from conventional refinery operations can be mentioned. Isomerization of alkylbenzenes include those of xylenes, diethylbenzenes, cymenes, and other di- and polyalkylbenzenes.

In carrying out isomerizations of isomerizible $C_4$ to $C_{20}$ hydrocarbons, contact between the catalyst and hydrocarbon charge is conducted at temperatures between about 0° and 250° C., preferably between about 25° and 150° C., at pressures between atmospheric and 25 atmospheres or more. The hydrocarbon is passed over the catalyst as a gas or liquid generally admixed with hydrogen, with an hourly space velocity generally between about 0.5 and 5.0. The resulting product is withdrawn from the reactor, and is separated by any suitable means such as fractional distillation. Any unreacted starting material may be recycled. The superacidic isomerization catalysts generally also cause concurrent cleavage reactions (cracking).

Alkylations can also be effectively carried out employing the catalysts of the present invention. Alkylation of alkylatable hydrocarbons such as paraffins or aromatics with olefins, alkyl halides, alcohols, and other alkylating agents can be effected in the presence of the catalyst at temperatures between about 0° to 200° C. and the pressure between about atmospheric and 30 atmosphere.

The catalysts of the present invention are also suitable for catalytic cracking of hydrocarbons. The hydrocarbon charge may comprise normal paraffins or complex mixtures of paraffins, naphthenes, and aromatics, such as they occur in petroleum, which is the feed normally used in commercial catalytic cracking units. Hydrocarbon cracking utilizing catalysts of the present invention can be conducted at temperatures ranging between 50° and 250° C. and pressures from atmospheric to 50 atmospheres or higher. Presence of hydrogen (hydrocracking) can be applied to further prolong catalyst life and, thus, cause more efficient cracking operations. It is of particular significance that the catalysts of the present invention, when based on non-reducible halides, such as tantalum and niobium pentafluoride, are very effective hydrocracking catalysts, which are not affected by the presence of sulfur and other impurities, and which normally cause rapid reactivation of conventional cracking catalysts. In view of the need of increased utilization of "heavy" petroleums and lower grade crudes, the new catalysts and process of this invention is of considerable commercial significance.

Other applications of the catalysts of present invention towards additional conversions of hydrocarbons should be apparent to those skilled in the art of hydrocarbon chemistry.

The perfluorinated alkanesulfonic acids used in the catalysts of this invention can be prepared by various methods, such as for example, by the use of electrofluorination in preparing the corresponding perfluorinated alkanesulfonyl fluorides, which subsequently can be hydrolyzed to the related alkanesulfonic acids, according to the JOURNAL OF THE CHEMICAL SOCIETY (London) (1957) pages 2640–2645. Alternate methods of preparation include reaction of perfluorinated alkyl iodides ($R_fI$) through their Grignard reaction with sulfur dioxide or addition of sulfonyl halides to perfluorinated olefines.

The scope of the invention will be further described in connection with the following examples, which are set forth for purposes of illustration only and are not to be construed as limited to the scope of the invention in any manner.

EXAMPLE 1

10 g of a perfluorinated hexanesulfonic acid $C_6F_{13}SO_3H$ was deposited via vacuum sublimination at 100° C. over 75 g of fluoridated alumina (containing about 40% by weight fluorine). 5 g of $SbF_5$ was subsequently distilled in a dry nitrogen stream onto the catalyst. The catalyst thus obtained was heated in vacuum to 100° C. for a period of 6 hours until no loss in weight or pressure increase was observed indicating complete bonding of the SbF$_5$.

10 g of this catalyst was charged into a fluid bed reactor and n-heptane (reagent grade 99+% purity) admixed with hydrogen was passed continuously over the catalyst at 80° C. reaction temperature. Isomerization accompanied by some cracking was observed. Cracking can be further reduced by carrying out the reaction in the presence of increased concentration of hydrogen gas. Results are summarized in Table 1.

EXAMPLE 2

10 g of perfluorinated decanesulfonic acid C$_{10}$F$_{21}$SO$_3$H was vacuum distilled onto 5 of TaF$_5$, which was subsequently deposited via vacuum distillation in dry N$_2$ atmosphere unto 50 g of fluoridated alumina; the catalyst, which was subsequently heated and maintained at 150° C. in vacuum for 6 hours until no loss of weight or pressure increase was observed, indicating complete bonding of the catalyst.

The catalyst was used in the isomerization of n-heptane in the same manner as described in Example 1. Results are summarized in Table 1.

EXAMPLE 3

A catalyst composition was prepared in the same manner as described in Example 2, except that NbF$_5$ was substituted for TaF$_5$.

The catalyst was used in the isomerization of n-heptane as described in Example 1. The results are summarized in Table I.

TABLE I

|  | Ex. I<br>C$_6$F$_{13}$SO$_3$H—SbF$_5$ | Ex. II<br>C$_{10}$F$_{21}$SO$_3$H—TaF$_5$ | Ex. III<br>C$_{10}$F$_{21}$SO$_3$H—Nb$_5$ |
|---|---|---|---|
| n-heptane | 56.8 | 67.6 | 71.2 |
| propane | 0.1 | 0.1 | 0.1 |
| methylpropane | 9.1 | 7.4 | 7.2 |
| butane | 0.9 | 0.6 | 0.3 |
| methylbutane | 6.1 | 5.4 | 5.0 |
| pentane | 0.2 | 0.1 | 0.1 |
| 2,2-diemthylbutane | 0.1 | 0.1 | 0.1 |
| 2,3-dimethylbutane | 0.8 | 0.6 | 0.5 |
| 3-methylpentane | 0.1 | 0.1 | 0.1 |
| hexane | 0.1 | 0.1 | 0.1 |
| 2,2-dimethylpentane | 0.8 | 0.2 | 0.1 |
| 2,4-dimethylpentane | 6.9 | 4.9 | 4.8 |
| 2,2,3-trimethylbutane | 2.1 | 0.7 | 0.5 |
| 3,3-dimethylpentane | 1.1 | 0.3 | 0.2 |
| 2-methylhexane | 6.2 | 4.6 | 4.1 |
| 2,3-dimethylpentane | 2.4 | 1.8 | 0.8 |
| 3-methylhexane | 3.9 | 3.1 | 2.6 |
| C$_8$ and others | 2.3 | 2.3 | 2.2 |

EXAMPLE 4

A catalyst obtained in the same manner described in Example 1 was used at a reaction temperature of 70° C. in the isomerization of n-hexane. Table II shows the result of a typical composition of the isomerization products.

TABLE II

| isobutane | 2.1 | 2,2-dimethylpentane | 1.0 |
|---|---|---|---|
| n-butane | 0.2 | 2,4-dimethylpentane | 1.8 |
| 2,2-dimethylpropane | tr | 2,2,3-trimethylbutane | 0.8 |

TABLE II-continued

| 2-methylbutane | 8.1 | 3,3-dimethylpentane | 0.7 |
|---|---|---|---|
| n-pentane | 0.9 | 2-methylhexane | 2.1 |
| 2,2-dimethylbutane | 16.9 | 2,3-dimethylpentane | 0.9 |
| 2,3-dimethylbutane | 2.6 | 3-methylhexane | 1.6 |
| 2-methylpentane | 6.9 | 3-ethylpentane | tr |
| 3-methylpentane | 3.3 | n-heptane | tr |
| n-hexane | 41.6 | methylcyclohexane | tr |
|  |  | other products | 8.5 |

EXAMPLES 5–7

A catalyst described in Example 3 was used for the alkylation of alkanes with olefins. Specific examples studied were the reactions of butane with butene-1, (Example 5); isobutane with ethylene (Example 6); and n-butane with propylene (Example 7). Results obtained are summarized in Table IV.

TABLE III

|  | Ex. 5<br>n-Butane-butene-1 | Ex. 6<br>Isobutane-ethylene | Ex. 7<br>n-Butane-propylene |
|---|---|---|---|
| Butanes plus pentanes | 58 | 18 | 49 |
| Hexanes | 5 |  | 10 |
| 2,2-dimethylbutane |  | 25 |  |
| 2,3-dimethylbutane |  | 5 |  |
| 2-methylpentane |  | 9 |  |
| 3-methylpentane |  | 5 |  |
| n-hexane |  | 4 |  |
| Heptanes | 3 |  |  |
| 2,2-dimethylpentane |  |  | 0.5 |
| 2,4-dimethylpentane |  |  | 5 |
| 2,2,3-trimethylbutane |  |  | 3 |
| 3,3-dimethylpentane |  |  | 0.5 |
| 2-methylhexane |  |  | 10 |
| 2,3-dimethylpentane |  |  | 5 |
| 3-methylhexane |  |  | 6 |
| Octanes |  |  | 11 |
| Trimethylpentanes |  | 3 |  |
| Dimethylhexanes |  | 14 |  |
| Methylheptanes |  | 7 |  |
| Heptanes plus higher |  |  | 34 |

EXAMPLE 8

The catalyst prepared in Example 2 was used in a continuous flow reactor at 140° C. in the ethylation of benzene with ethylene utilizing a flow ratio of benzene to ethylene of 1.5 to 1.0 mmol/min. The results are summarized in Table IV.

TABLE IV

| Time, Hours | % Ethylbenzene | % Diethylbenzenes |
|---|---|---|
| 1 | 28 | 8 |
| 2 | 36 | 9 |
| 3 | 34 | 8 |
| 6 | 29 | 7 |
| 8 | 30 | 8 |
| 16 | 32 | 9 |
| 24 | 33 | 8 |

EXAMPLE 9

Transethylation of benzene with diethylbenzenes was carried out over a catalyst prepared from perfluorinated hexanesulfonic acid treated with TaF$_5$, as described in the previous examples. 5 g of the catalyst was charged into the continuous flow reactor and the reaction carried out at 180° with a feed ratio of 1 mml/min. benzene, 0.4 mml/m ethylbenzene.

TABLE V

| Time, Hours | % Ethylbenzene |
|---|---|
| 1 | 16 |
| 2 | 28 |
| 3 | 30 |
| 4 | 30 |
| 6 | 28 |
| 8 | 31 |
| 12 | 33 |
| 24 | 32 |

While the invention has been described in connection with preferred embodiments, it is not intended to limit the invention to the particular forms set forth, but, on the contrary, it is intended to cover such alternatives, modifications, and equivalents as may be included within the spirit and scope of the invention as defined by the appended claims.

I claim:

1. An isomerization process which comprises continuously passing an isomerizable C$_4$ to C$_{30}$ hydrocarbon over a catalyst comprising a C$_{10}$ to C$_{18}$ perfluorinated alkanesulfonic acid which is deposited or absorbed upon a suitable support and having bonded thereto from between about 1 and 50 percent by weight of the total catalyst composition of a Lewis acid fluoride selected from the elements of Group IIA, IIIA, IVB, VA, VB, or VIB of the Periodic Table to effect a continuous heterogeneous flow isomerization of the hydrocarbon at a temperature between about 0° and 250° C. and at a pressure between atmospheric and about 25 atmospheres.

2. The process of claim 1 wherein the hydrocarbon is a striaght chain paraffin, a branched chain paraffin, a cycloparaffin, a napthene, or an alkyl aromatic compound.

3. The process of claim 1 which further comprises admixing the hydrocarbon with hydrogen before passing the hydrocarbon over the catalyst.

4. The process of claim 1 wherein the hydrocarbon is passed over the catalyst at an hourly space velocity of between about 0.5 and 5.

5. The process of claim 1 which further comprises withdrawing the isomer products from the reaction, separating unreacted starting material from said isomer products, and recycling the separated unreacted starting material.

6. The process of claim 1 wherein the temperature ranges from about 25° and 150° C.

7. The process of claim 1 wherein the Lewis acid fluoride is antimony pentafluoride, tantalum pentafluoride, or niobium pentafluoride.

8. An alkylation process which comprises continuously passing an alkylatable hydrocarbon and an alkylating agent over a catalyst comprising a C$_{10}$ to C$_{18}$ perfluorinated alkanesulfonic acid which is deposited or absorbed upon a suitable support and having bonded thereto from between about 1 and 50 percent by weight of the total catalyst composition of a Lewis acid floride selected from the elements of Group IIA, IIIA, IVB, VA, VB, or VIB of the Periodic Table to effect a continuous heterogeneous flow alkylation of the hydrocarbon at a temperature between about 50° and 250° C. and at a pressure between atmospheric and about 50 atmospheres.

9. The process of claim 8 wherein the alkylatable hydrocarbon is a paraffin or aromatic compound.

10. The process of claim 8 wherein the alkylating agent is an alkyl halide, an olefin, or an alcohol.

11. The process of claim 8 which further comprises introducing hydrogen into the process along with the alkylatable hydrocarbon and alkylating agent to prolong the life of the catalyst.

12. The process of claim 8 wherein the Lewis acid fluoride is antimony pentafluoride, tantalum pentafluoride, or niobium pentafluoride.

* * * * *